(12) United States Patent
Wilcox et al.

(10) Patent No.: US 7,976,468 B2
(45) Date of Patent: *Jul. 12, 2011

(54) SOFT TISSUE DIAGNOSTIC APPARATUS AND METHOD

(75) Inventors: Ariel Wilcox, Dixmont, ME (US); Charles E. Tarr, Brooksville, ME (US); Judith A. Hilton, Bangor, ME (US)

(73) Assignee: Signal Insight Inc., Freeport, ME (US)

( * ) Notice: Subject to any disclaimer, the term of this patent is extended or adjusted under 35 U.S.C. 154(b) by 297 days.

This patent is subject to a terminal disclaimer.

(21) Appl. No.: 11/716,625

(22) Filed: Mar. 12, 2007

(65) Prior Publication Data

US 2007/0156049 A1 Jul. 5, 2007

Related U.S. Application Data

(63) Continuation of application No. 10/873,517, filed on Jun. 23, 2004, now Pat. No. 7,261,693, which is a continuation of application No. 09/987,197, filed on Nov. 13, 2001, now abandoned, which is a continuation-in-part of application No. 09/562,964, filed on May 3, 2000, now Pat. No. 6,364,849.

(60) Provisional application No. 60/132,169, filed on May 3, 1999, provisional application No. 60/274,614, filed on Mar. 12, 2001.

(51) Int. Cl.
*A61B 8/00* (2006.01)

(52) U.S. Cl. ........ 600/439; 600/552; 600/586; 600/454; 600/455; 600/456; 600/437; 600/443; 600/447; 601/2

(58) Field of Classification Search .......... 600/437–439, 600/443, 447, 454–456, 552, 586; 601/2
See application file for complete search history.

(56) References Cited

U.S. PATENT DOCUMENTS

| | | | | | |
|---|---|---|---|---|---|
| 3,880,145 | A | * | 4/1975 | Blick | 600/485 |
| 4,269,193 | A | * | 5/1981 | Eckerle | 600/485 |
| 5,669,388 | A | * | 9/1997 | Vilkomerson | 600/455 |
| 5,678,565 | A | | 10/1997 | Sarvazyan | |
| 6,364,849 | B1 | | 4/2002 | Wilcox | |

* cited by examiner

*Primary Examiner* — Tse Chen
*Assistant Examiner* — John F Ramirez
(74) *Attorney, Agent, or Firm* — Jeffrey L. Costellia; Nixon Peabody, LLP

(57) ABSTRACT

A soft tissue diagnostic apparatus for diagnosis of stress and injury in anatomical soft tissue by detecting the response of the soft tissue to acoustic energy and a method of detecting soft tissue damage or stress and treating the tissue. An acoustic transmitter transmits excitation acoustic energy toward a target area of soft tissue of a subject. An acoustic receiver receives responsive acoustic energy generated by the soft tissue in response to the excitation acoustic energy transmitted by the acoustic transmitter and generates an output signal representative of the response of the soft tissue to the excitation acoustic energy. An analyzer receives the output signal of the acoustic receiver and provides an indication of at least one of stress and injury in the soft tissue based on the output signal. Areas of stress are inhibited to find the origin of soft tissue pain.

43 Claims, 9 Drawing Sheets

SOFT TISSUE DIAGNOSTIC APPARATUS AND METHOD

RELATED APPLICATION DATA

This application is a continuation of U.S. patent application Ser. No. 10/873,517 filed on Jun. 23, 2004 now U.S. Pat. No. 7,261,693, the disclosure of which is incorporated herein by reference, which is a continuation of application Ser. No. 09/987,197 filed on Nov. 13, 2001, now abandoned, which is a continuation-in-part of application Ser. No. 09/562,964 filed on May 3, 2000, now U.S. Pat. No. 6,364,849, which claims benefit from provisional application Ser. No. 60/132,169 filed on May 3, 1999. This application also claims benefit of Provisional Application Ser. No. 60/274,614 filed on Mar. 12, 2001, the disclosure of which is incorporated herein by reference.

BACKGROUND OF THE INVENTION

1. Field of the Invention

The invention relates to diagnosis and treatment of soft tissue pain. More particularly, the invention is a method and apparatus for measuring responses of soft tissue subject to acoustic stimulation, processing the response, and interpreting the response to indicate the location of stress and/or injury in soft tissue and for verifying the effectiveness of treatment of soft tissue.

2. Description of the Related Art

Existing techniques for diagnosis of the source of pain in soft tissue are relatively subjective and inaccurate. Typically, clinicians rely upon responses to patient questionnaires, medical histories, and subjective observation to diagnose the source of pain in soft tissue. These tools are inherently imprecise even when used in a meticulous manner. Several expensive technologies have been applied to diagnosis of the source of soft tissue pain. For example, magnetic resonance imaging (MRI), x-rays, and computerized tomography (CT) are known noninvasive technologies. Invasive technologies include nerve blocks, probes, and the like. Even when utilizing these technologies, results are frequently inaccurate or inconclusive. Multiple studies have shown that x-rays have little value in routine examination of the source of soft tissue pain. Even MRI is now only rarely recommended in back pain, since surgery based on such imaging has had a high failure rate. Moreover, the demonstration of abnormal scans and x-rays in people who lack back pain symptoms casts serious doubt upon the value of these technologies in soft tissue diagnosis.

Other diagnostics have little value in diagnosing the source of soft tissue pain. Nerve conduction studies and electromyography are indicated for detection of nerve damage only at advanced stages. Measurement devices for indicators of tissue mobility or tension are limited in scope and applicability. Ultrasound may image large muscle tears and can depict certain tissue, but not specifically pain or stress in tissue. Nerve blocks may identify an area of pain but are not suited for routine evaluation because skilled administration of injected anesthetic agents are required and risk factors are elevated. Blood flow analyses also have limited relevance to soft tissue pain.

Serum and saliva analyses for substances associated with pain have been used to diagnose the source of pain. However, protocols, norms, and standardization of sampling and processing techniques have yet to be established for such analyses. One theory is that visualization of chronic neck-shoulder pain can be achieved through the quantification of lowered microcirculation. However, this quantification requires the insertion of optical laser-Doppler single-fibers into two muscle sites concurrently with increased static contraction using electromyography. Of course, this method, even If proven to be accurate, is painful and has a high risk factor.

It is known to use acoustic energy to determine physical properties of various nonliving materials. Also, acoustic energy has been used In various medical applications. For example, U.S. Pat. No. 5,795,311 discloses an apparatus for treating tissue by imparting acoustic energy thereto. U.S. Pat. No. 5,458,130 discloses an apparatus which applies ultrasonic energy for measuring bone density, and strength, and for treating musculoskeletal tissue using a complex signal generator and processing system. U.S. Pat. No. 4,509,524 discloses a device for characterizing tissue based on reflected ultrasonic waves. U.S. Pat. No. 4,819,621 discloses an apparatus for detecting cavitation in tissue injuries by detection of a reflected acoustic signal. U.S. Pat. No. 4,216,766 discloses an apparatus for treating tissue by applying acoustic energy at the resonant frequency of a gas filled cavity surrounding the tissue to be treated. U.S. Pat. No. 5,115,808 discloses an apparatus for measuring the velocity of acoustic signals in tissue for determining the shear elastic properties of the tissue. U.S. Pat. No. 5,545,124 discloses a method for alleviating pain by charging tissue with acoustic shockwaves. However, the prior art does not permit reliable detection of stress in soft tissue through noninvasive measures. Accordingly, the prior art fails to provide a method or apparatus for diagnosing the source of pain due to soft tissue damage or stress.

Therefore, a vast area of difficult and often intractable syndromes of pain defy quantification and thus are difficult to treat in a reliable manner. Conventional diagnostic investigation often yields limited or equivocal findings, and involves expensive, painful and indirect methods. It follows that, therapeutic measures are compromised by this lack of resources.

The phrase "soft tissue" as used herein includes muscles, ligaments, connective tissue and fascia, nerve and blood vessel walls, and other essential structures of the body. Diagnostic designations relating to these tissues include chronic pain, strain, musculoskeletal pain and injury, myofascial pain and injury, benign, non-malignant, or idiopathic pain; myalgia, fibrositis, or fibromylalgia; repetitive strain injury (RSI) or overuse injury, including carpal tunnel syndrome (CTS), epicondylitis, tennis elbow, bursitis and tendinitis, temporomandibular joint disorder (TMD or TMJ), orofacial and neck pain, several types of headache, pelvic pain of unknown etiology, and back pain (all of which are included in the classification of "soft tissue pain" as used herein). The onset of soft tissue pain may have had an identifiable traumatic component but the duration of the pain often far exceeds the expected physiological process of recovery. Gross damage and disease processes are often absent with soft tissue pain.

The economic impact of soft tissue pain is reported by such studies as those of the annual combined cost of back pain-related medical care and disability compensation, which alone may reach $50 billion annually in the U.S. Back pain affects about 31 million Americans, is the leading cause of activity limitation in young adults, and generates annual U.S. productivity losses in the range of $28 billion. Incidence of tension-type headaches has been reported as high as 48.9%, with numerous annual lost workdays and days of decreased effectiveness at work, home, or school. Neck pain occurred at a 34% rate in one study. These statistics are representative of the magnitude of the of soft tissue pain which is severely hampered by lack of efficient diagnosis. It is frequently difficult to differentiate between specific conditions which benefit from surgery and those which do not. Despite due care in evaluation, surgery fails a significant percentage of patients who do not obtain relief and whose condition may even worsen. Conversely, surgical interventions performed for non-pain reasons are themselves a recognized cause of chronic soft tissue pain which is difficult to identify.

SUMMARY OF THE INVENTION

It is an object of the invention to facilitate detection of abnormalities, such as stress and damage of soft tissue in a non-invasive manner.

To achieve these objects, a first aspect of the invention is a soft tissue diagnostic apparatus for detecting abnormalities in anatomical soft tissue by detecting the response of the soft tissue to acoustic energy. Said apparatus is comprised of comprising an acoustic transmitter configured to transmit excitation acoustic energy toward a target area of soft tissue of a subject, an acoustic receiver configured to receive responsive acoustic energy generated by the soft tissue in response to the excitation acoustic energy transmitted by said acoustic transmitter, said acoustic receiver generating an output signal representative of the response of the soft tissue to the excitation acoustic energy transmitted by said acoustic transmitter. Said apparatus also contains an analyzer coupled to said acoustic receiver to receive the output signal of said acoustic receiver and to provide an indication signal of at least one of stress and injury in said soft tissue based on said output signal of said acoustic receiver, and a pressure device configured to apply pressure to areas of the soft tissue having a maximum response of the soft tissue to the excitation acoustic energy of transmitted by said acoustic transmitter.

A second aspect of the invention is a method of detecting abnormalities in anatomical soft tissue by detecting the response of the soft tissue to acoustic energy. The method comprises: (a) determining an area of soft tissue having a localized characterized acoustic response; (b) applying pressure to the area of maximum responsive acoustic energy to inhibit acoustic response of the area while simultaneously transmitting excitation acoustic energy toward the area and receiving responsive acoustic energy generated by the area; (c) repeating said steps (a) and (b) for each of the plural target areas while applying pressure to all previously detected target areas; (d) when all responses have been inhibited by application of pressure, a location of characteristic acoustic response will be identified that is not responsive to efforts to inhibit it, i.e., the inhibitory effort will not exceed the maximum previously applied pressure. This determines the target area as a treatment location.

A third aspect of the invention is a device for detecting abnormalities in soft tissue comprising, a housing, an acoustic transmitter disposed in said housing and configured to transmit excitation acoustic energy toward a target area of soft tissue of a subject, an acoustic receiver disposed in said housing and configured to receive responsive acoustic energy generated by the soft tissue in response to the excitation acoustic energy transmitted by said acoustic transmitter, said acoustic receiver generating an output signal representative of the response of the soft tissue to the excitation acoustic energy transmitted by said acoustic transmitter, and a pressure device operatively coupled to said housing and configured to apply pressure to the target area of the soft tissue.

BRIEF DESCRIPTION OF THE DRAWING

The invention will be described through a preferred embodiment and the attached drawing in which.

DETAILED DESCRIPTION OF THE PREFERRED EMBODIMENT

Figure 1:
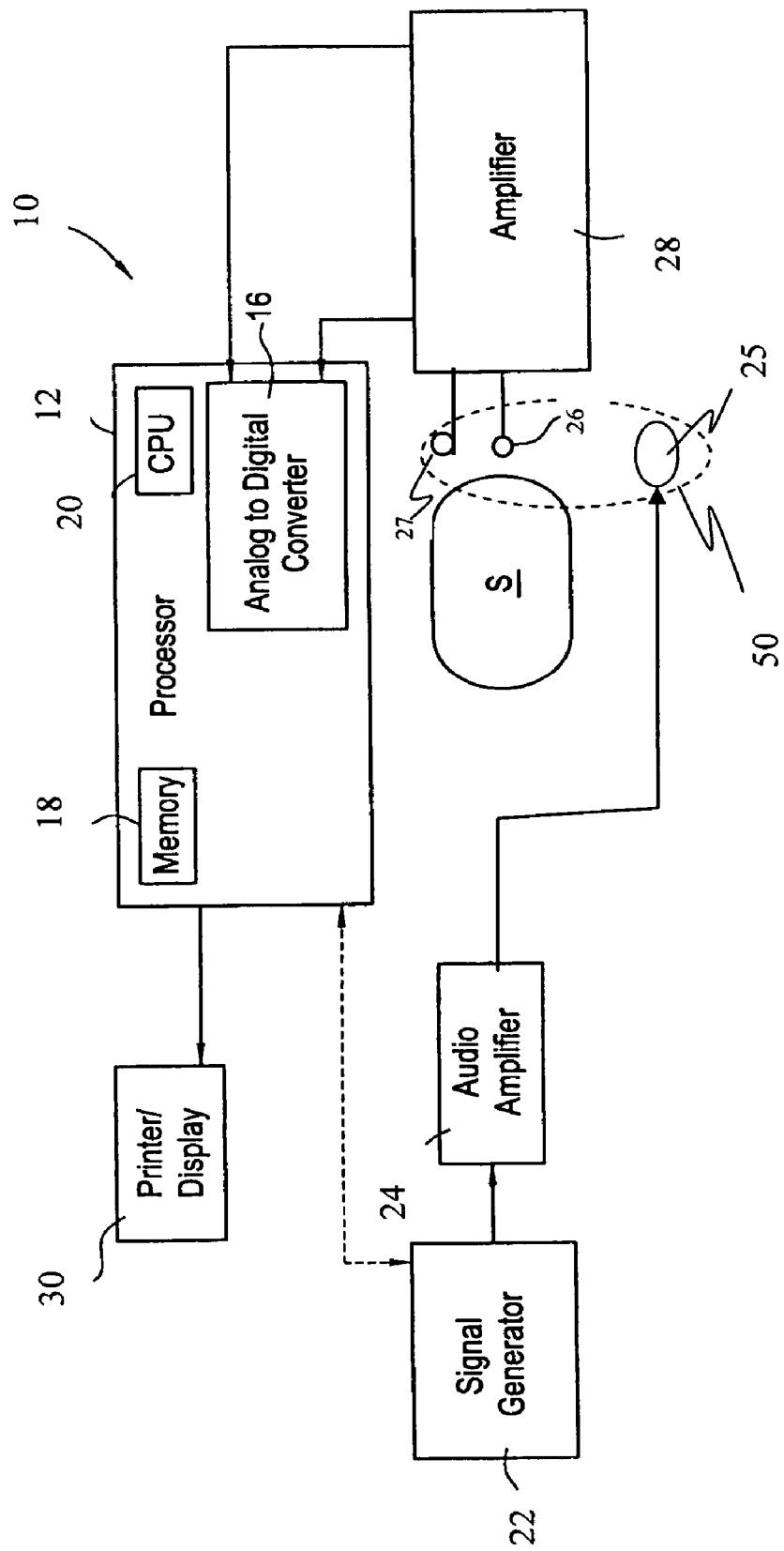
FIG. 1 is a block diagram of a diagnostic apparatus of the preferred embodiment.

Scientific research has identified a model called "tensegrity which provides form, flexibility, communication, response, strength and resilience throughout the body's structure. The tensegrity structural components of the body, from DNA and cytoskeleton to entire cells and tissues, exhibit characteristic resonant frequencies of vibration. Studies have shown that the matrix of tensegrity maintains a force balance which provides a means to integrate mechanics and biochemistry at the molecular level. Physical forces are converted into biological responses when mechanically induced information is transmitted through the molecular and cellular complexes. The tensegrity networks of the body mediate this mechanotransduction; their organizations have been found to function as coupled harmonic oscillators. Such mechanotransduction significantly influences cell function, tissue growth and remodeling, gene expression, and participates with ion channels, signaling molecules, proteins, lipids, chemical transmitters and more.

At the tissue level, ligaments, fascia, muscles, bones, and blood vessels demonstrate tensegrity structure and properties in their individual and intertwined organizations. These components constantly receive input and perform or adapt in response, demonstrating mechanical communication and information processing. The nervous system is another type of communication network involved with responses to internal or external stresses. In located areas or centrally in the brain, neural tissue plays a large role in processing information, directing action and maintaining homeostasis. Neurally mediated responses such as voluntary movement, involuntary functions, and self protective reactions involve signal transfer processes. This communication is facilitated by the tensegrity structure on the cellular level and through nerve pathways as well as through tensegrity relationships between the musculoskeletal and other tissue participants.

The body's interactions with its internal and external environment involve a high level of complexity and coordination, yet the integrated network responds instantly. This is possible because the body is always in readiness at a level of internal tone called pre-stress, an isometric/elastic state which supports immediate mechanical responsiveness, in addition to essential balance, decompression, form and stability. Elevation of the normal pre-stress threshold interferes with the resiliency of the network. Translated to the soft tissues, excessive pre-stress causes restriction, stiffness, compression, and asymmetrical organization. Many cellular processes are altered or affected, including transmembrane receptors which participate in pain generation.

Perpetuation and proliferation of these stresses result in tissue restriction and pathological adhesions, causing immobility and pain. Inflammatory responses may also be stimulated, producing pain signaling substances. Nerves may be irritated through traction or compression as well as biochemical transmission, providing yet another link between mechanical tensional dysfunctions and pain generation. Conduction of forces can lead to elevated stresses that are isolated or, more likely, networked into a domino effect, being recruited into patterns of reaction, reinforcement and compensation. Dysfunction can proliferate throughout the tensegrity system. Therefore, diagnosis needs to be site-specific to the latent reaction that is perpetuating the strain and elevated pre-stress and it needs to be sensitive to the hierarchical compensatory and stabilizing strain relationships.

The parent application, the disclosure of which is incorporated herein by reference, discloses the detection of "barriers" and "anchors". Barriers are areas of soft tissue stress reaction that exhibit tensional restriction of mobility when assessed through palpation and other techniques. Barriers are the result of irritation and strain patterns originating from stress reactions of the tissue at the anchor location. Anchors, sometimes referred to as "interfaces" herein, are the ultimate origin of the soft tissue injury and as such need to be precisely identified for accurate diagnosis of the injury etiology and effective treatment results.

As disclosed in the parent application, the alteration of density and tensile qualities of soft tissue due to stress changes the impedance and/or dispersion thereof, thus affecting acoustic properties thereof. The persistent state of elevated pre-stress that remains following excessive demand may significantly participate in the condition commonly identified as soft tissue injury. Thus, altered tensional dynamics of the soft tissue produce idiosyncratic acoustical responses which can be utilized as diagnostic indicators.

The preferred embodiment quantifies acoustical responses of soft tissue to locate specific sites of tensional involvement and thus diagnose soft tissue stress or injury and to confirm the effectiveness of treatment thereof. Accordingly, the preferred embodiment drastically reduces the level of skill required to locate and treat soft tissue injuries.

FIG. 1 is a block diagram of a diagnostic apparatus according to a preferred embodiment of the invention. Apparatus 10 includes processor 12 as an analyzer. In the preferred embodiment processor 12 is a microprocessor based digital device, such as a personal computer. However, any type of analyzer can be used, such as an analog signal processor, or the like. Processor 12 includes multichannel analog to digital converter A/D 16. Of course, if processor 12 is analog, A/D 16 can be omitted and replaced by appropriate analog signal interfaces. Processor 12 of the preferred embodiment also has memory device 18, which can include one or more of a random access memory (RAM), a magnetic disk memory device, an optical memory device, or the like, for storing instructions of a control program. Processor 12 also has central processing unit (CPU) 20 for executing the instructions of the control program. Display 30 is coupled to processor 12 to display test results, variables, and the like.

Signal generator 22 is configured to generate an electrical signal of predetermined frequency as described below. The operator can adjust the frequency of the electrical signal or select a progression of frequencies to be generated by signal generator 22 in a known manner. Amplifier 24 receives the electrical signal from signal generator 22 to drive speaker 25 serving as an audio source. The audio source can be any transducer capable of producing an acoustic vibrational signal in response to electrical impulses or other signals, such as a cone speaker, a planar driver speaker, or a piezoelectric device. Also, the signal provided to the audio source can be of any appropriate type. Signal generator 22, amplifier 24, and speaker 25 constitute an acoustic transmitter in the preferred embodiment. However, the acoustic transmitter can be any device for transmitting acoustic energy, such as a tuning fork, a tone generator, or the like. Preferably, the audio source is highly directional to be capable of isolating particular soft tissue areas.

Audio sensor 26 and audio sensor 27 are coupled to A/D 16 of processor 12 through multi channel amplifier 28. Audio sensors 26 and 27 and amplifier 28 constitute an acoustic receiver of the preferred embodiment. However, the acoustic receiver can be any device for receiving acoustic energy and distinguishing characteristics thereof, such as a selective resonator, the operators ear, or the like. Sensors 26 and 27 can be microphones, styli, piezoelectric vibration sensors, optical motion sensors, accelerometers, or any other transducer capable of directly or indirectly sensing acoustic energy or motion and outputting a signal related thereto. Sensors 26 and 27 can be contact sensors or non-contact sensors. As will be seen below, sensor 26 serves to detect soft tissue response to acoustic energy and sensor 27 serves to detect background acoustic energy. Processor 12 can include the necessary processing circuitry or software to eliminate background noise, such as 60 Hz hum and noise detection by sensor 27, to eliminate any undesired phase or amplitude of the received signal, or to otherwise, linearize, manipulate, transition or enhance the signals received from multi-channel amplifier 28. For example, if microphones or any other non contact sensor are used as audio sensors 26 and 27, it may be necessary to correct for the phase delay of the audio signal due to the finite velocity if sound to avoid errors due to direct coupling between speaker 25 and audio sensor 26. Preferably, audio sensor 26 is directional to a high degree to minimize noise and environmental effects. Signal generator 22, amplifier 24 and amplifier 28 can be incorporated in processor 12. For example, a conventional sound card or interface can be used if processor 12 is a personal computer.

Figure 2:
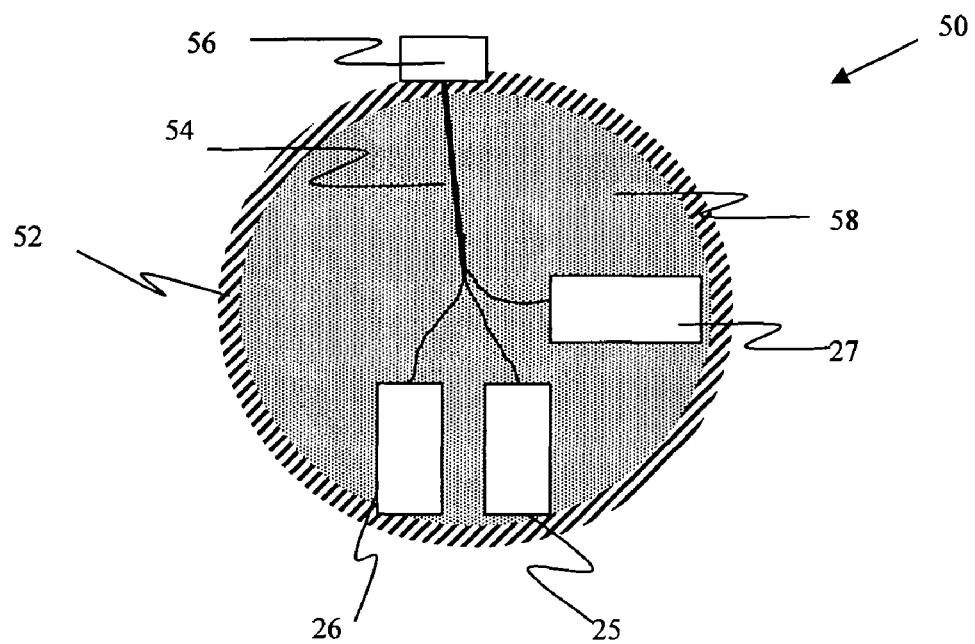
FIG. 2 is a sectional view of a stabilizer of the preferred embodiment.

In the preferred embodiment, sensor 26, sensor 27 and speaker 25 are integrated into stabilizer 50 as illustrated in FIGS. 1 and 2. Stabilizer 50 includes housing 52 of a substantially spherical shape in the preferred embodiment. Preferably housing 52 is somewhat flexible to permit the surface thereof to conform to various anatomical surfaces. Sensor 26, sensor 27, and speaker 25 are electrically connected to other components, as disclosed above, through wiring harness 54 and connector 56. Note that sensor 27 is remote from a portion of stabilizer 50, the bottom portion in FIG. 1, that will be placed in contact with tissue. Insulating material 58 is disposed in housing 52 to isolate the components in housing 52. As will become apparent below, it is necessary that stabilizer 50 be sufficient mass to inhibit the characteristic acoustic response. For example. Insulating material 58 can be of a material that imparts such mass to stabilizer 50. Stabilizer 50 can also include a separate pressure member, such as a weight, a pressure strap or the like, to exert the requisite pressure on tissue as discussed below.

To use diagnostic apparatus 10 for diagnosis of soft tissue damage or stress, soft tissue S of a patient is placed proximate speaker 25 to be in the path of acoustic energy generated by speaker 25, as illustrated in FIG. 1. In the preferred embodiment stabilizer 50 can be placed directly on tissue. Soft tissue S is then stimulated with various frequencies of acoustic energy from speaker 25 to determine a frequency of maximum response amplitude as detected by sensors 26. The frequency of maximum response can be used for further testing. For example, frequencies between 100 and 1000 Hz can be used at 70-90 db.

A barrier is then located using known techniques, such as the palpation technique disclosed in the parent application. Stabilizer 50 is placed on the barrier site so that sensor 26 is opposite the tissue thereof. Sensors 26 and 27 are monitored while the tone is generated and the output signal thereof is recorded in memory 18 and processed as described below.

Applicant conducted tests using diagnostic apparatus 10 of the preferred embodiment to confirm the effectiveness thereof and the repeatability of data acquired thereby. In the tests, sites of characteristic acoustic response indicating tension were located by a trained therapist using conventional techniques. However, these sites can be located using the apparatus of the preferred embodiment. Applicant has found that there can be plural areas of soft tissue tension, i.e. multiple sites of characteristic acoustic responses identifiable in the body of one patient who presents for diagnosis and/or treatment. Application of sufficient pressure to the location of tension will reduce the tension and characteristic tension acoustic response at that area. This is referred to as "inhibition" or "inhibiting" herein. Inhibition also enhances the elucidation of acoustic detection of other areas which relate to the soft tissue dysfunction and the location of the interface which is the site of neural responses that are the origin of pain as described below.

Applicant postulates that there are locations in the soft tissue that contain the neural and other activities that produce soft tissue dysfunction (the "interface"). The interface creates compensatory and reactive tensions in other locations and structures that are affected to cope with the dysfunction. These compensatory tensions have a characteristic acoustic response. The response and tension of each can be reduced and minimized by light to moderate pressure applied by a weighted object, such as stabilizer 50, placed on top of the body part or an object (collectively referred to as the "pressure device") placed on or underneath the body part and pushing on the body part. When the acoustic responses and tensions are sufficiently inhibited by pressure at the appropriate locations, the generalized acoustic responses are minimized to the point of near total disappearance. When this has been achieved, a site of unique acoustic response, the interface, will be detectable at the location of the origin of pain, making it apparent and amenable for treatment and alleviation.

The procedure for finding the interface can be carried out in the following manner. First, an area of characteristic acoustic response indicating tension is determined through frequency and location of maximum acoustic response using techniques disclosed above. The pressure device is then applied in the general area, stimulating the frequency and adjusting position of the device until the acoustic response is minimized. This step is repeated until all acoustic responses at other sites are identified and blocked as described above. This may or may not be accomplished by locating the sites in order of magnitude of response. At this point, a location of unique response can be determined using the acoustic response characteristics disclosed above. This location of unique response, the interface, is the area to be treated using physical therapy. The following is a description of testing using stabilizer 30 in connection with diagnostic apparatus 10.

Figure 3:
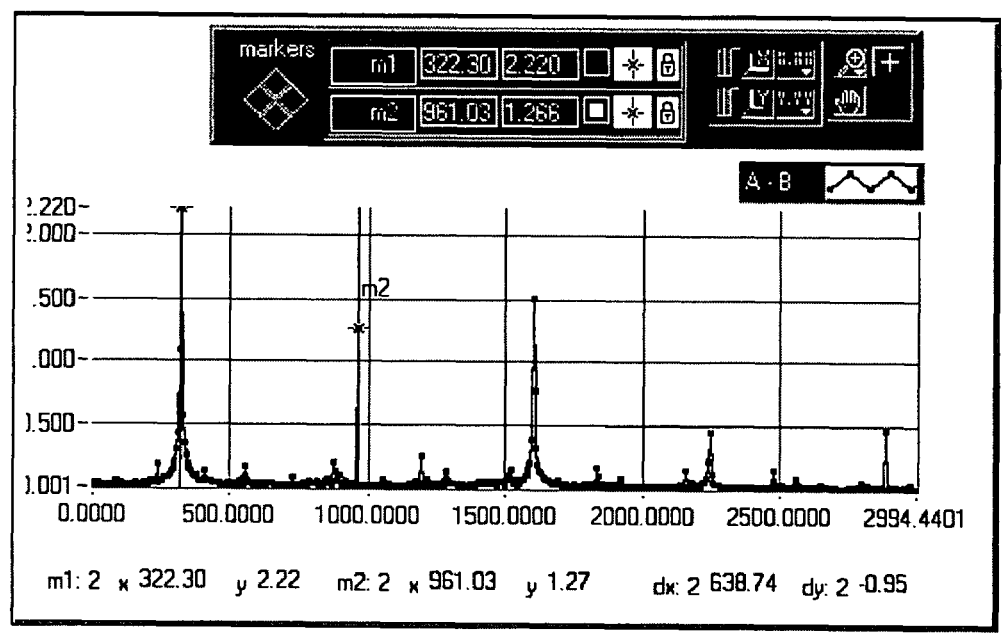
FIG. 3-8 are graphs of the response of soft tissue under various conditions when tested with the preferred embodiments.

A subject was laid on a bodywork table and locations of soft tissue stress were identified using a therapist and a tuning fork in the manner described in provisional application Ser. No. 60/132,169, the disclosure of which is incorporated herein by reference. A first location of the greatest stress identified in this manner was then inhibited by placing stabilizer 50, having a weight of approx. 2-lb. (i.e., of sufficient mass to inhibit the characteristic acoustic response), on the location of greatest stress, and acoustic response of the tissue was measured. The graph of this data is shown in FIG. 3. It can be seen that, at the fundamental stimulation frequency of 322.30 Hz the resulting voltage of the response signal was 2.22 volts. The voltage of the response signal at the first harmonic, 961.03 Hz, was 1.27 volts.

Figure 4:
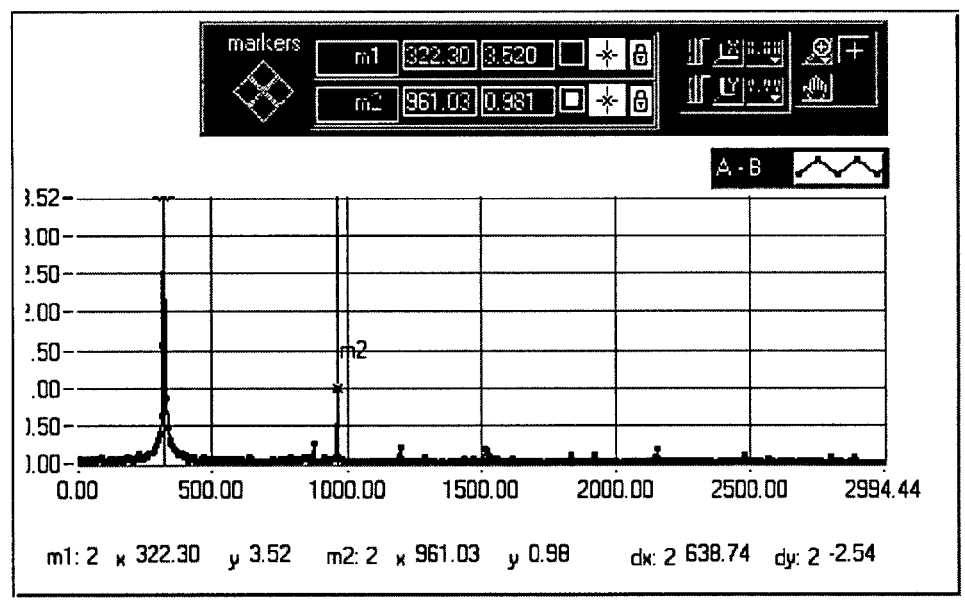

Stabilizer 50 was removed from the first location and an inhibition weight of about 2 lbs. was placed on the first location to inhibit response of the first location. A therapist then identified a second location of soft tissue stress. This site was also inhibited, and acoustic response was measured, using stabilizer 50. FIG. 4 is a graph of this response. It can be seen that, at the fundamental stimulation frequency of 322.30 hz the resulting voltage of the response signal was 3.52 volts. The voltage of the response signal at the first harmonic, 961.03 hz, was 0.98 volts.

Figure 5:
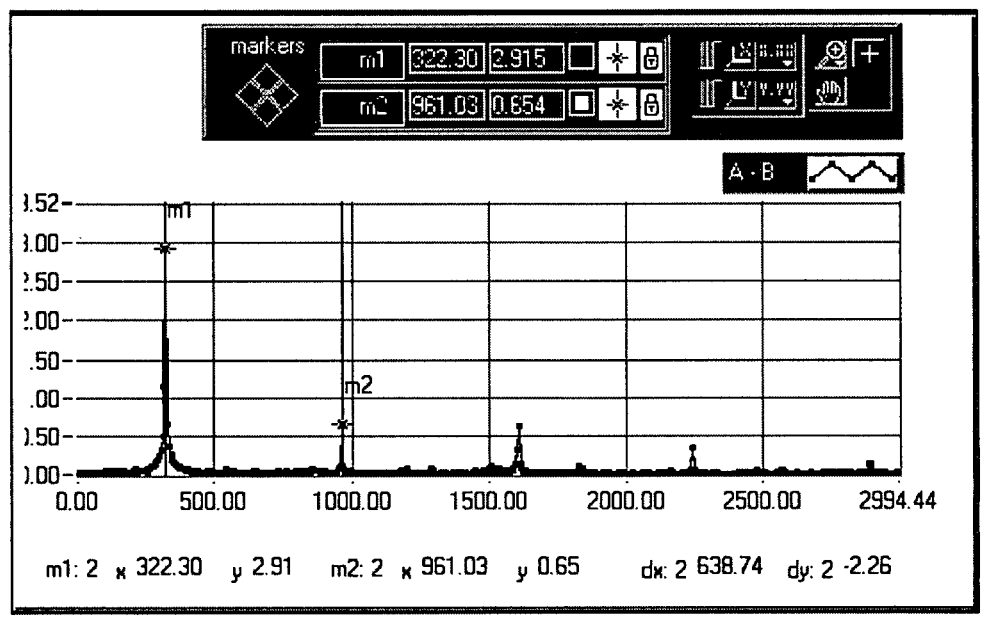
Figure 6:
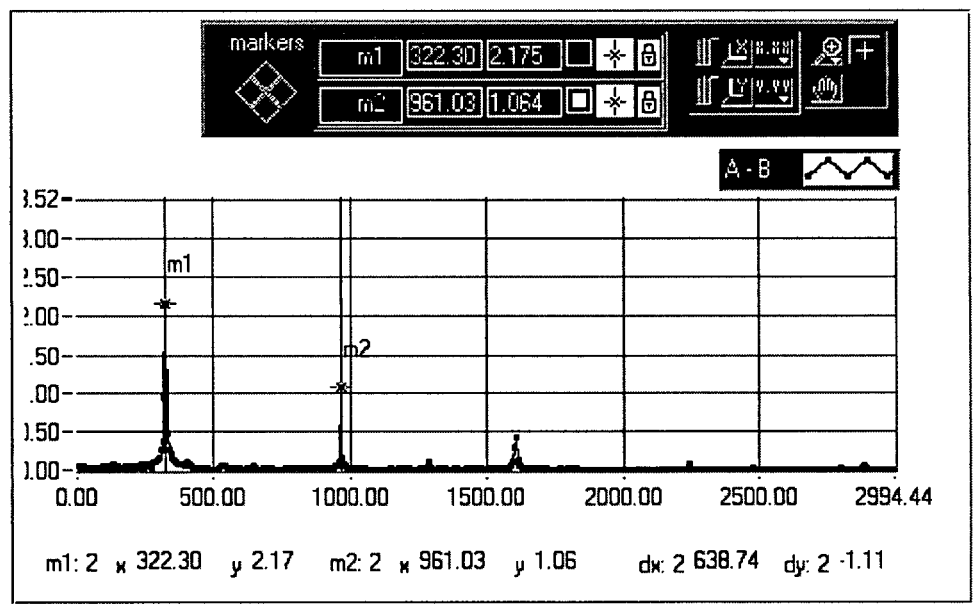

With the first and second locations inhibited, a third location of stress was identified by a therapist. While inhibiting the first and second locations, measurements were taken at the third location using stabilizer 50. FIG. 5 is a graph of the uninhibited response at the third location with the other locations being uninhibited. It can be seen that, at the fundamental stimulation frequency of 322.30 Hz, the resulting voltage of the response signal was 2.91 volts. The voltage of the response signal at the second harmonic, 961.03 Hz, was 0.65 volts. FIG. 6 is a graph of the inhibited response at the third location with the other locations being inhibited. It can be seen that, at the fundamental stimulation frequency of 322.30 Hz, the resulting voltage of the response signal was 2.17 volts. The voltage of the response signal at the first harmonic, 961.03 hz, was 1.06 volts.

Figure 7:
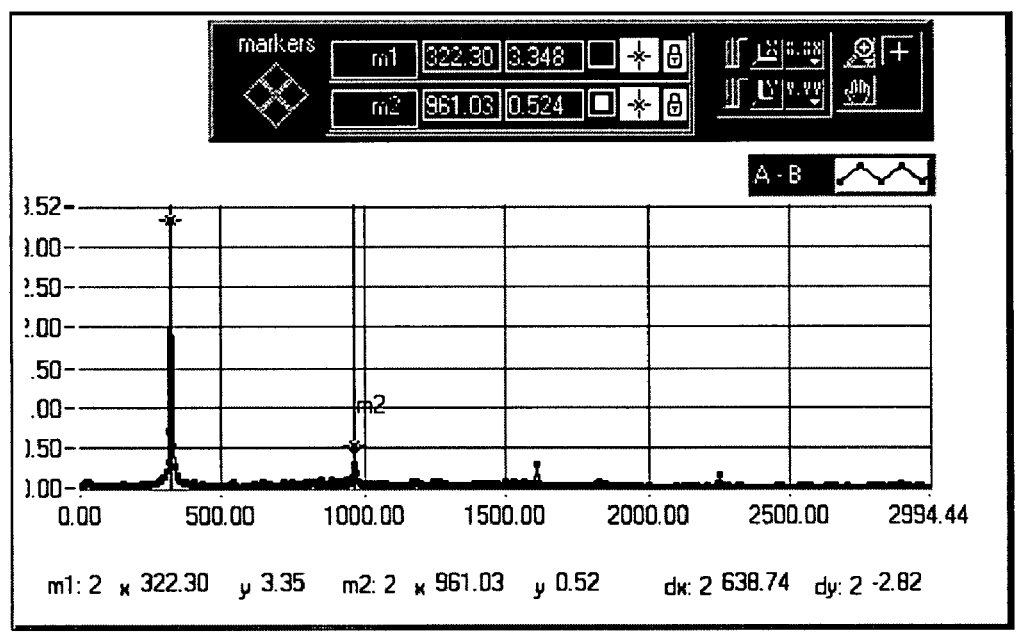
Figure 8:
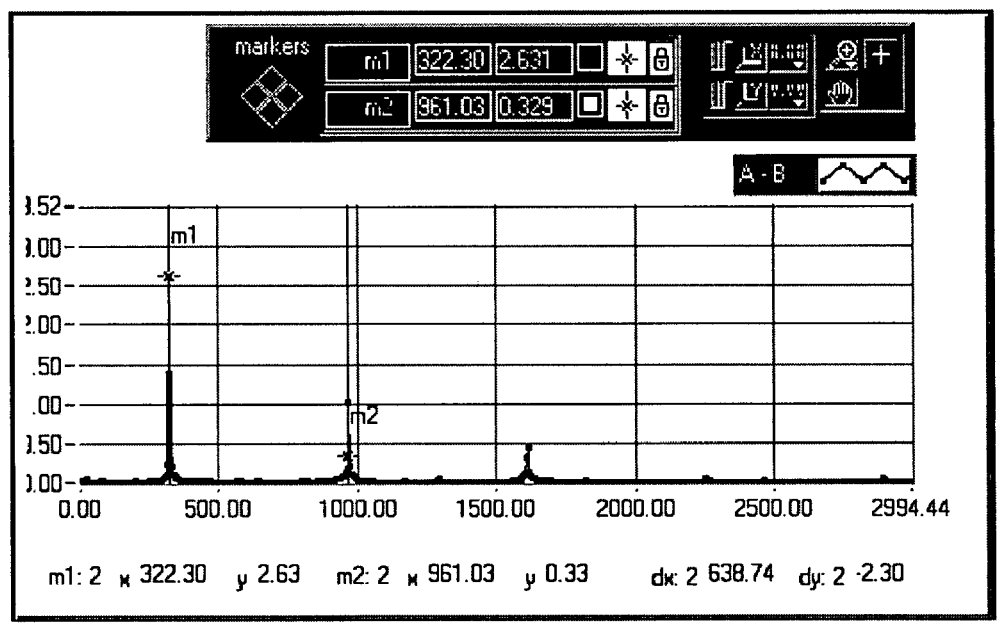

The first, second and third locations were inhibited and the therapist could identify only one other location, the fourth location in this case, of high soft tissue stress. This final location of stress is the interface discussed above. Uninhibited acoustic response was measured at the fourth location using stabilizer 50 with all other locations inhibited. FIG. 7 is a graph of the response at the fourth location with other locations inhibited. It can be seen that, at the fundamental stimulation frequency, the resulting voltage of the response signal was 3.35 volts. The voltage of the response signal at the second harmonic was 0.52 volts. All the inhibition weights were then removed from the subject and the measurement at the fourth site was repeated with stabilizer 50. FIG. 8 is a graph of the response at the fourth location with other locations not inhibited. It can be seen that, at the fundamental stimulation frequency, the resulting voltage of the response signal was 2.63 volts. The voltage of the response signal at the first harmonic was 0.33 volts.

As shown in the graphs of FIGS. 4-8, the voltage measured at the non-interface locations decreased when inhibition pressure was applied to other locations. However, the interface site voltage was larger when all other locations were inhibited, and decreased when the inhibition pressure at other locations was removed. It can be seen that the interface, while being the origin of pain and the best location for treatment is only ascertainable after location and inhibition of other stress locations.

Figure 9:
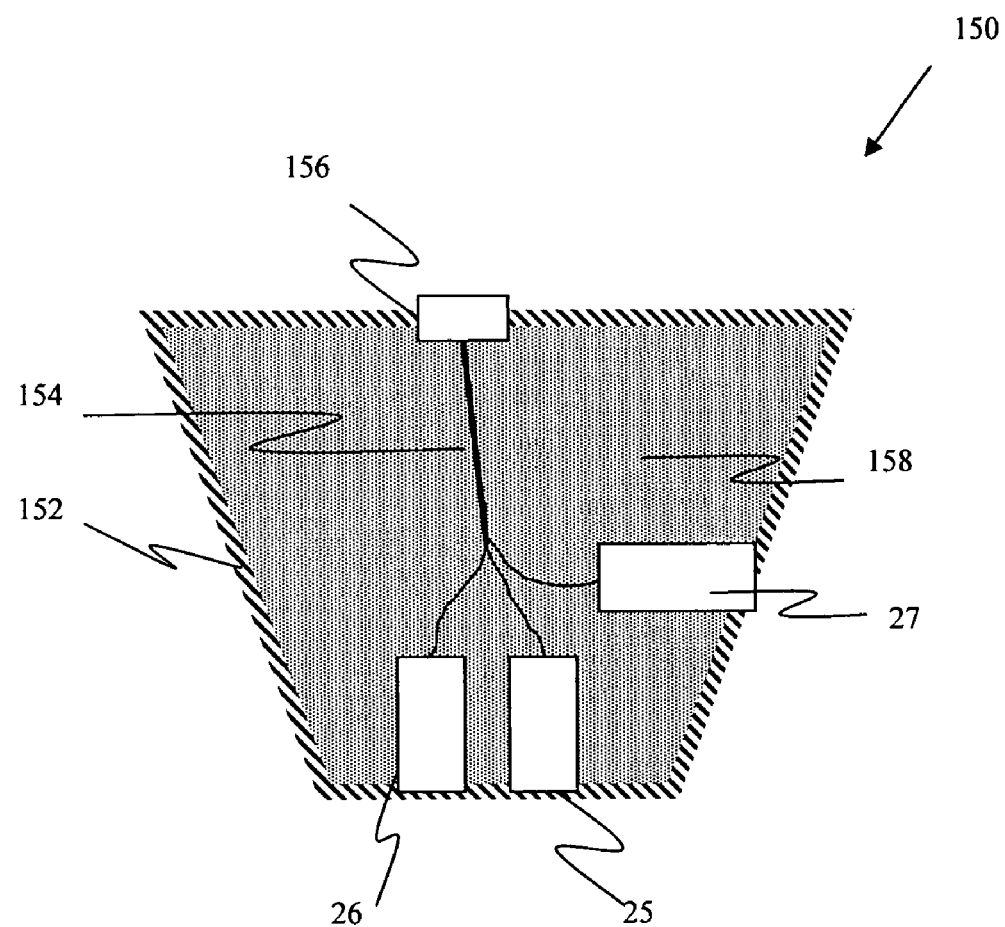
FIG. 9 is a sectional view of an alternative stabilizer of the preferred embodiment.

FIG. 9 illustrates and alternative stabilizer 150 in which housing 152 is in the shape of an inverted pyramid. This shape presents a flat surface to opposes soft tissue and may be better suited to large somewhat planar anatomical surfaces. All other aspect of stabilizer 150 are similar to stabilizer 50 and like elements are labeled with similar reference numerals have the prefix of "1." The stabilizer can be used to gather information regarding each location of soft tissue stress identified by a therapist or the sensor instrument disclosed in the parent application. The data could be used to monitor the continued inhibition of each stabilized location, and can be used to characterize locations of soft tissue stress and their interrelation with each other.

As noted above, the acoustic transmitter and/or receiver can be integrated into the pressure device. In such a case, the source and sensors can contact the tissue. Alternatively, separate contact or non-contact transmitters and/or receivers can be used. The electrical signal generated by the signal generator can be of a constant frequency or of a variable frequency over time to find the frequency of maximum response. The frequency can be varied manually in response to operator input or through the control program in a predetermined manner. For example, the frequency can initially be 100 Hz and can be varied in increments of 50 Hz up to 1 kHZ. Applicant has found that most stressed or damaged soft tissue will respond to a frequency within this range. Of course, the range of frequencies, the incremental change, and the rate of change can be varied based on various practical considerations. Also, the amplitude of the acoustic energy signal can be varied as needed.

The audio sensor can be positioned to detect vibration (i.e., responsive acoustic energy) of particular portions of the soft tissue, in response to the acoustic energy generated by the speaker. For example, particular nerves, muscles, ligaments, or the like can be investigated. The audio sensors can be placed over the soft tissue percutaneously or can be directed toward the soft tissue depending on whether the audio sensor is of a type that senses in a contact or non-contact state. Audio sensors employing ultrasound techniques can be used to detect Doppler effects due to resonance of interior organs, blood vessels, or other tissue to permit diagnosis of internal tissue damage or stress. Additional sensors can be used depending on the application and desired resolution of results. Any type of processing can be used to distinguish the response signal of abnormal tissue from that of normal tissue.

As noted above, applicant has found that stressed or damaged soft tissue will respond to a frequency of excitation acoustic energy in a manner that is distinguishable from the response of normalized tissue. Accordingly, stressed and damaged tissue can be distinguished from normalized tissue and accurately located and treated. Also, the effectiveness of treatment can be verified by measuring acoustic response after treatment. These capabilities are especially desirable because often the stressed or damaged tissue is remote from the apparent location of pain indicated by the patient. Testing can provide baselines of normalized tissue to be compared with results of tissue being tested. For example, testing may indicate that a particular area of a patient's hand, in a normalized state, has a particular acoustic profile, transfer function or power spectrum. This can be compared with test results to determine if tissue is stressed or damaged. The control program of the processor can correct any non linearities based on calibration with a known element used in place of the soft tissue.

Living tissue has a complex structure, and not surprisingly, is highly dispersive at acoustic frequencies. To elucidate the difference in acoustic response of stressed and nonstressed sites, the control program of the processor should include instructions for performing processing of data, i.e., response signals, collected by the sensor. Any appropriate processing can be accomplished on the response signals.

Any type of acoustic transmitter and receiver can be used. The analyzer can be configured to accomplish various processing of the sensor signals, such as filtering, transforming, shifting, amplifying, and attenuating. Any type of acoustic sensor can be used. The sensors can be disposed to sense acoustic response of various locations. The invention can be used on any type of soft tissue.

While the invention has been described through a preferred embodiment, various modifications can be made without departing from the scope of the invention as defined by the appended claims.

What is claimed is:

1. A soft tissue diagnostic apparatus for detecting abnormalities in anatomical soft tissue by detecting the response of the soft tissue to acoustic energy comprising:
   an acoustic transmitter configured to transmit excitation acoustic energy toward a target area of soft tissue of a subject;
   an acoustic receiver configured to receive responsive acoustic energy generated by the soft tissue in response to the excitation acoustic energy transmitted by said acoustic transmitter, said acoustic receiver generating an output signal representative of the response of the soft tissue to the excitation acoustic energy transmitted by said acoustic transmitter;
   an analyzer coupled to said acoustic receiver to receive the output signal of said acoustic receiver and to provide an indication signal of at least one of altered behavior and mechanical properties which are associated with stress and injury in said soft tissue based on said output signal of said acoustic receiver; and
   a pressure device configured to be physically pressed against areas of soft tissue to thereby apply pressure to areas of the soft tissue having a maximum response of the soft tissue to the excitation acoustic energy transmitted by said acoustic transmitter, and to thereby inhibit at least one of tension and a characteristic tension acoustic response.

2. An apparatus as recited in claim 1, wherein said transmitter comprises a first transducer said receiver comprises a second transducer and wherein said first transducer and said second transducer are integrated with said pressure device.

3. An apparatus as recited in claim 1, wherein said pressure device is a weight that is separate from said transmitter and said receiver.

4. An apparatus as recited in claim 2, wherein said receiver further comprises a third transducer integrated with said pressure and operative to receive background acoustic energy, and wherein said analyzer is operative to subtract a signal from said third transducer from a signal from said second transducer to correct at least one of background noise and minimize other instrumental artifacts.

5. A device for detecting abnormalities in soft tissue comprising:
   a housing;
   an acoustic transmitter disposed in said housing and configured to transmit excitation acoustic energy toward a target area of soft tissue of a subject;
   an acoustic receiver disposed in said housing and configured to receive responsive acoustic energy generated by the soft tissue in response to the excitation acoustic energy transmitted by said acoustic transmitter, said acoustic receiver generating an output signal representative of the behavior and mechanical properties which are indicated by the response of the soft tissue to the excitation acoustic energy transmitted by said acoustic transmitter; and
   a pressure device operatively coupled to said housing and configured to be physically pressed against areas of soft tissue to thereby apply pressure to areas of the soft tissue having a maximum response of the soft tissue to the excitation acoustic energy transmitted by said acoustic transmitter, and to thereby inhibit at least one of tension and a characteristic tension acoustic response.

6. A device as recited in claim 5, wherein said pressure device is a mass disposed in said housing to impart substantial weight to the device.

7. A device as recited in claim 5, wherein said receiver further comprises a background acoustic receiver disposed in said housing and operative to receive at least one of background acoustic energy and instrumental artifacts.

8. An apparatus as recited in claim 1, further comprising a digital processor with a multichannel analog to digital converter or an analog processor with analog signal interfaces.

9. An apparatus as recited in claim 1, where the acoustic transmitter is at least one of a cone speaker, a planar driver speaker, or a piezoelectric device, a tuning fork, or a tone generator.

10. An apparatus as recited in claim 1, where the acoustic receiver is at least one of a selective resonator, the operator's ear, microphones, styli, piezoelectric vibration sensors, optical motion sensors, accelerometers.

11. An apparatus as recited in claim 1, wherein the acoustic receiver may consist of contact sensors or non-contact sensors.

12. An apparatus as recited in claim 8, where said digital or analog processor includes at least one of circuitry or software to eliminate background noise.

13. An apparatus as recited in claim 12, wherein said background noise elimination includes one or more of removing 60 Hz hum and linearizing, manipulation, transitioning, enhancing the signals received, or eliminating phase delay.

14. An apparatus as recited in claim 1, wherein the acoustic receiver is integrated into a stabilizer.

15. An apparatus as recited in claim 14, wherein the acoustic receiver is spherical.

16. An apparatus as recited in claim 1, wherein said excitation acoustic energy has an intensity of between 70 and 90 dB at frequencies between 100 and 1000 Hz.

17. An apparatus as recited in claim 1, which uses a barrier using the palpation technique.

18. An apparatus as recited in claim 1, wherein said pressure device is operative to successively apply pressure in regions to reveal an interface with unique acoustic response.

19. An apparatus as recited in claim 18 wherein said interface is found by progressively finding areas of maximum acoustic response, then eliminating them using stabilizers.

20. An apparatus as recited in claim 1, wherein the excitation activation energy ranges between 100 and 1000 Hz.

21. An apparatus as recited in claim 1, wherein said analyzer operates percutaneously, in contact with the skin, or not in contact with the skin.

22. An apparatus as recited in claim 1, wherein the analyzer can be configured to accomplish various processing of the sensor signals, such as filtering, transforming, shifting, amplifying, and attenuating.

23. An apparatus as recited in claim 1, wherein at least one of the tension and the characteristic acoustic response is inhibited while the excitation activation energy is sent and the pressure device applies pressure near an area not of interest.

24. An apparatus as recited in claim 1, wherein the acoustic response is increased while the excitation activation energy is sent near an area of interest and the pressure device applies pressure near an area that is not of interest.

25. An apparatus as recited in claim 1, further comprising a display which outputs information about the soft tissue to a user.

26. A device as recited in claim 5, wherein the device includes a digital processor with a multichannel analog to digital converter or an analog processor with analog signal interfaces.

27. A device as recited in claim 5, wherein the acoustic transmitter is at least one of a cone speaker, a planar driver speaker, or a piezoelectric device, a tuning fork, or a tone generator.

28. A device as recited in claim 5, wherein the acoustic receiver is at least one of a selective resonator, the operator's ear, microphones, styli, piezoelectric vibration sensors, optical motion sensors, accelerometers.

29. A device as recited in claim 5, wherein the acoustic receiver may consist of contact sensors or non-contact sensors.

30. A device as recited in claim 5, wherein said digital or analog processor includes at least one of circuitry or software to eliminate background noise.

31. A device as recited in claim 30 wherein said background noise elimination includes one or more of removing 60 Hz hum and linearizing, manipulation, transitioning, enhancing the signals received, or eliminating phase delay.

32. A device as recited in claim 5, wherein the acoustic receiver is integrated into a stabilizer.

33. A device as recited in claim 32, wherein the acoustic receiver is spherical.

34. A device as recited in claim 5, wherein said excitation acoustic energy has an intensity of between 70 and 90 dB at frequencies between 100 and 1000 Hz.

35. A device as recited in claim 5, which uses a barrier using the palpation technique.

36. A device as recited in claim 5, wherein said pressure device is used to successively apply pressure in regions to reveal an interface with unique acoustic response.

37. A device as recited in claim 36 wherein said interface is found by progressively finding areas of maximum acoustic response, then eliminating them using stabilizers.

38. A device as recited in claim 5, wherein the excitation activation energy ranges between 100 and 1000 Hz.

39. A device as recited in claim 5, wherein said analyzer operates percutaneously, in contact with the skin, or not in contact with the skin.

40. A device as recited in claim 5, wherein the analyzer can be configured to accomplish various processing of the sensor signals, such as filtering, transforming, shifting, amplifying, and attenuating.

41. A device as recited in claim 5, wherein at least one of the tension and the characteristic acoustic response is inhibited while the excitation activation energy is sent and the pressure device applies pressure near an area not of interest.

42. A device as recited in claim 5, wherein the acoustic response is increased while the excitation activation energy is sent near an area of interest and the pressure device applies pressure near an area that is not of interest.

43. A device as recited in claim 5, further comprising a display which outputs information about the soft tissue to a user.

* * * * *